United States Patent
Visser et al.

(10) Patent No.: US 10,723,681 B2
(45) Date of Patent: Jul. 28, 2020

(54) PROCESS FOR MANUFACTURING PURIFIED GLYCEROL

(71) Applicant: PURAC BIOCHEM B.V., Gorinchem (NL)

(72) Inventors: Diana Visser, Gorinchem (NL); André Banier De Haan, Gorinchem (NL); Wijnand Raphaël Terlouw, Gorinchem (NL); David Sanchez Garcia, Gorinchem (NL)

(73) Assignee: PURAC BIOCHEM B.V., Gorinchem (NL)

( * ) Notice: Subject to any disclaimer, the term of this patent is extended or adjusted under 35 U.S.C. 154(b) by 613 days.

(21) Appl. No.: 15/324,180

(22) PCT Filed: Jul. 9, 2015

(86) PCT No.: PCT/EP2015/065681
§ 371 (c)(1),
(2) Date: Jan. 5, 2017

(87) PCT Pub. No.: WO2016/005490
PCT Pub. Date: Jan. 14, 2016

(65) Prior Publication Data
US 2017/0174595 A1 Jun. 22, 2017

(30) Foreign Application Priority Data
Jul. 9, 2014 (EP) .................................. 14176263

(51) Int. Cl.
| C07C 29/80 | (2006.01) |
| C12P 7/52 | (2006.01) |
| C07C 29/86 | (2006.01) |
| C12P 7/20 | (2006.01) |
| C12P 7/18 | (2006.01) |

(52) U.S. Cl.
CPC .............. *C07C 29/80* (2013.01); *C07C 29/86* (2013.01); *C12P 7/18* (2013.01); *C12P 7/20* (2013.01); *C12P 7/52* (2013.01)

(58) Field of Classification Search
None
See application file for complete search history.

(56) References Cited
U.S. PATENT DOCUMENTS
8,124,814 B2 * 2/2012 Krafft .................... C07C 29/62
568/844

FOREIGN PATENT DOCUMENTS

| CN | 101 748 163 A | 6/2010 |
| CN | 102703530 A | 10/2012 |
| DE | 102007002129 A1 | 7/2008 |
| EP | 2486807 A1 | 8/2012 |
| WO | 2009/098301 A1 | 8/2009 |
| WO | 2010/118716 A1 | 10/2010 |
| WO | 2013/033665 A1 | 3/2013 |
| WO | 2013/079785 A1 | 6/2013 |
| WO | 2013/082309 A1 | 6/2013 |
| WO | 2014/084938 A1 | 6/2014 |

OTHER PUBLICATIONS

Zhang A et al, "Propionic acid production from glycerol by metabolically engineered Propionibacterium acidipropionici", Process Biochemistry, vol. 44, No. 12, Dec. 1, 2009, pp. 1346-1351.
Pin Pin Oh et al, "A review on conventional technologies and emerging process intensification (PI) methods for biodiesel production", Renewable and Sustainable Energy Reviews, vol. 16, No. 7, May 5, 2012, pp. 5131-5145.
Helwani Z et al, "Technologies for production of biodiesel focusing on green catalytic techniques: A review", Fuel Processing Technology, vol. 90, No. 12, Dec. 1, 2009, pp. 1502-1504.
Gutierrez L F et al, "Process of integration possibilities for biodiesel production from palm oil using ethanol obtained from lignocellulosic residues of oil palm industry," Bioresource Technology, vol. 100, No. 3, Feb. 1, 2009, pp. 1227-1237.
Sep. 21, 2015 International Search Report issued in International Patent Application No. PCT/EP2015/065681.
Sep. 21, 2015 Written Opinion issued in International Patent Application No. PCT/EP2015/065681.

* cited by examiner

*Primary Examiner* — Heidi Reese
(74) *Attorney, Agent, or Firm* — Oliff PLC

(57) ABSTRACT

A process for manufacturing purified glycerol including the steps of providing a starting glycerol fraction comprising glycerol, water, and fatty acid methyl esters, subjecting the glycerol fraction to a partial evaporation to form an evaporated fraction including glycerol, water, and fatty acid methyl esters, and a remainder fraction including glycerol, condensing the evaporated fraction to form a liquid, subjecting the liquid evaporated fraction including glycerol, water, and fatty acid methyl esters to a liquid-liquid separation step, resulting in the formation of a fatty acid methyl ester fraction and a glycerol-based fraction including glycerol and water. The process makes it possible to efficiently separate the fatty acid methyl esters from glycerol, without the need for complete glycerol distillation. Also provides glycerol fractions suitable for use as carbon source in fermentation processes, without problems in down-stream processing, and without the need for cost-intensive purification steps for the glycerol.

13 Claims, 1 Drawing Sheet

PROCESS FOR MANUFACTURING PURIFIED GLYCEROL

The present invention pertains to a process for manufacturing purified glycerol. The invention also pertains to a fermentation process using a glycerol-containing material as carbon source, more specifically, a process for manufacturing diols or carboxylic acid salts via a fermentation process using a glycerol-containing material as carbon source.

Glycerol-based materials are becoming increasingly available, as glycerol is a side product from the manufacture of biodiesel. Biodiesel is a sustainable and renewable fuel produced from various oils and fats. Conventional feedstock for biodiesel manufacture include vegetable and animal lipid materials, more specifically frying and cooking fats, vegetable edible and non-edible oils, such as corn oil, soy oil, palm oil, animal fats from food processing, industrial greases and solvents, and other renewable sources, such as oil from algae and oils and fats produced by fermentation. In the process of manufacturing biodiesel, the oils and fats are decomposed to form fatty acid (esters) and glycerol.

Glycerol has been used as starting material in fermentation processes.

For example, CN101748163 describes a fermentation process for the manufacture of calcium propionate having glycerol as carbon source.

CN102703530 describes a variation on the process of CN101748163 above using a different microorganism.

A. Zhang and S. T. Yang (Process Biochemistry 44 (2009) 1346-1351) also describes a fermentation process for the manufacture of propionate using glycerol as single carbon source.

A problem occurring in the use of glycerol as starting material in a fermentation process for the manufacturing carboxylic acid salts or diols is the following.

Glycerol resulting from biodiesel manufacture, sometimes also indicated as crude glycerol, contains various contaminants including salts and so-called matter organic non-glycerol, also indicated as MONG. Such glycerol can, e.g., comprises 40-80 wt. % of glycerol. 5-10 wt. % of salts, and the balance further components such as methanol, water, and 5-40 wt. % of MONG. MONG also includes fatty acid methyl esters, also indicated as FAME, which is biodiesel.

Purified glycerol can, e.g., be obtained by distillation of crude glycerol in combination with a carbon treatment. While purified glycerol is a suitable starting material in a fermentation process, it has the disadvantage that it requires substantial energy input to carry out the necessary distillation steps. On the other hand, it has been found that if crude glycerol is used as starting material in a glycerol-based fermentation, problems occur. These problems are in particular found in downstream processing of the fermentation product, where it appears that product purity is insufficient.

There is therefore need in the art for a method for preparing a glycerol material suitable as carbon source for a fermentation where on the one hand the purification process requires relatively little energy while on the other hand problems in downstream processing are prevented. The present invention provides such a process.

The invention pertains to a process for manufacturing purified glycerol comprising the steps of
  providing a starting glycerol fraction comprising glycerol, water, and fatty acid methyl esters,
  subjecting the glycerol fraction to a partial evaporation to form an evaporated fraction comprising glycerol, water, and fatty acid methyl esters, and a remainder fraction comprising glycerol,
  condensing the evaporated fraction to form a liquid,
  subjecting the liquid evaporated fraction comprising glycerol, water, and fatty acid methyl esters to a liquid-liquid separation step, resulting in the formation of a fatty acid methyl ester fraction and a glycerol-based fraction comprising glycerol and water.

It has been found that the process according to the invention makes it possible to efficiently separate the fatty acid methyl esters from the glycerol, without the need for complete glycerol distillation. The process according to the invention also provides glycerol fractions suitable for use as carbon source in fermentation processes without problems in down-stream processing, and without the need for cost-intensive purification steps for the glycerol.

It is noted that methods for processing crude glycerol have been described in the art. However, these references describe processes comprise energy intensive processing steps such as distillation, or the glycerol fraction resulting therefrom is disposed of in a different manner, i.e. a manner not involving downstream processing of a fermentation product.

For example, WO2010/118716 describes a method for the continuous production of pure glycerol from crude glycerol containing potassium sulphate, by the steps of saponifying the organic impurities, evaporating the water, and separating the potassium sulphate by crystallization. The resulting glycerol product is used as combustion material.

DE102007002129 describes the use of disposable grade glycerol as starting material in biogas manufacture.

WO2009/098301 describes a method wherein crude glycerol is subjected to a distillation step to form a pure glycerol phase and a bottom product containing salt and glycerol, and contacting the bottom product containing salt and glycerol with water and an acid. The resulting product can be mixed with further organic material, and used as starting material in an anaerobic fermentation process for manufacture of methane.

EP2486807 describes a process for preparing nutritional, therapeutic, or organoleptic products from crude glycerol by growing yeast under aerobic conditions in a medium containing crude glycerol as carbon source. The resulting yeast product can be processed to obtain nutritional, therapeutic, or organoleptic products such as yeast paste.

WO2013/082309 describes a microorganism suitable for fermenting crude glycerol into organic molecules. No information is provided on downstream processing of the fermentation product.

The invention will be elucidated further below, with reference to the figures without being limited thereto or thereby.

Figure 1:
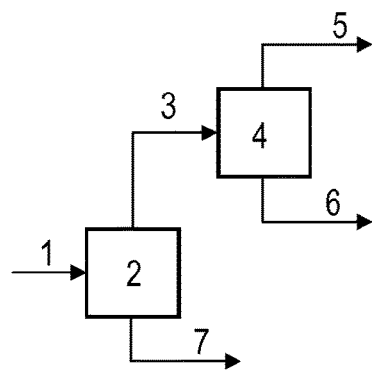
FIG. 1 illustrates a first embodiment of a process according to the invention.

The starting material in the present invention is a glycerol fraction comprising glycerol, water, and fatty acid methyl esters.

The glycerol fraction generally comprises water in an amount of 1-30 wt. %, in particular in an amount of 3-15 wt. %.

The glycerol fraction generally comprises fatty acid methyl esters in an amount of 1 to 20 wt. %, in particular in an amount of 5 to 15 wt. %. FAME can be determined by GC/MS in accordance with the method described in the Examples.

The glycerol fraction may comprise methanol, resulting from the biodiesel manufacturing process, where methanol is used in a transesterification reaction. The methanol content of the glycerol fraction is not critical, and can, e.g., be in the range of 0-10 wt. %, in particular 0-5 wt. %, more in particular 0-3 wt. %.

In one embodiment, glycerol fraction also comprises an inorganic salt. The inorganic salt, if present, will generally be present in an amount of 2-15 wt. %, in particular 5-10 wt. %. The nature of the inorganic salt will depend on the origin of the glycerol-containing fraction. It can, e.g., be one or more of earth alkali metal or alkali metal sulphates, nitrates, or chlorides. As will be discussed in more detail below, it has been found that one embodiment of the process according to the invention is of particular relevancy where the glycerol comprises substantial amounts of sulphate salts. Therefore, in one embodiment, the glycerol fraction has a inorganic sulphate salt content of 2-15 wt. %, in particular 5-10 wt. %.

In addition to the fatty acid methyl esters, the glycerol fraction may comprise further organic compounds. These compounds may vary widely in nature. In the present specification, they will be indicated as non-FAME MONG. MONG stands for so-called matter organic non-glycerol. Non-FAME MONG thus stands for matter organic non glycerol non fatty acid methylester.

The amount of non-FAME MONG in a glycerol fraction is defined as any organic matter with is not glycerol, methanol, or fatty acid methyl esters. It is calculated by determining the content of water, methanol, fatty acid methyl esters, inorganic salts, and glycerol in a glycerol fraction and subtracting these percentages from 100%. The non-FAME MONG content of the starting material of the present invention can vary within wide ranges, depending on the source of the glycerol fraction and any pretreatment steps. In one embodiment, the glycerol fraction comprises 0-35 wt. % of non-FAME MONG. In one embodiment the glycerol fraction can contain 0-10 wt. % of non-FAME MONG, in particular 0-5 wt. % of non-FAME MONG. In another embodiment, the glycerol fraction can comprise 5-35 wt. % of non-FAME MONG, in particular 5-20 wt. % of non-FAME MONG.

The glycerol content of the glycerol fraction used as starting material in the present invention may vary within wide ranges. It will generally be in the range of 40-95 wt. %, more in particular in the range of 50-90 wt. % glycerol. In one embodiment, the glycerol content in in the range of 55-85 wt. %, more specifically 60-80 wt. %.

The glycerol fraction used in the present invention can be derived from many sources. In one embodiment it is derived from crude glycerol derived from the manufacture of biodiesel.

In the process according to the invention, the starting glycerol fraction comprising glycerol, water, and fatty acid methyl esters is subjected to a partial evaporation to form an evaporated fraction comprising glycerol, water, and fatty acid methyl esters, and a remainder fraction comprising glycerol.

The crux of the partial evaporation step is that an evaporated fraction is formed comprising glycerol, water, fatty acid methyl esters, and methanol, if present.

The partial evaporation step can be carried out by methods known in the art. An example of a suitable partial evaporation method is flash evaporation, wherein the temperature of the starting glycerol fraction is increased under pressure, and pressure is then let off. A further example of a suitable partial evaporation method would be partial distillation. Preferably, the conditions during the partial evaporation step are selected such that of the water and methanol present in the starting glycerol fraction, at least 50%, in particular at least 70%, more in particular at least 85%, is evaporated. Even more in particular at least 90%, or at least 95% of the water and methanol present in the starting glycerol fraction is evaporated.

Of the FAME present in the starting glycerol fraction it is preferred that at least 50%, in particular at least 70%, more in particular at least 85%, is evaporated.

In the evaporation step, part of the glycerol is evaporated to the evaporated fraction, while part of the glycerol is in the remainder fraction. The amount of glycerol evaporated to the evaporated fraction is e.g., 10-50% of the glycerol present in the starting glycerol fraction, more specifically 20-40 wt. %.

It is within the scope of the skilled person to select a suitable method for effecting the partial evaporation, based on the guidelines specified above.

The composition of the evaporated fraction may, e.g., be as follows:

A glycerol content in the range of 25 to 90 wt. %, in particular 50 to 75 wt. %;

A fatty acid methyl ester content in the range of 1 to 20 wt. %, in particular 5 to 10 wt. %;

A water content in the range of 5 to 40 wt. %, in particular 10 to 20 wt. %;

A methanol content in the range of 0 to 6 wt. %, in particular 0 to 3 wt. %.

As compared to the starting glycerol fraction, the evaporated fraction will have a lower glycerol content, a higher water content, a higher FAME content, and if present, a higher methanol content.

The evaporated fraction is condensed to form a liquid. The condensation step will be done by methods known in the art, and generally encompasses temperature reduction.

In the liquid evaporated fraction, phase separation will occur between a (heavy) phase comprising glycerol and water, and a (light) fatty acid methyl ester phase. The liquid evaporated fraction is subjected to a liquid-liquid separation step, resulting in the formation of a fatty acid methyl ester fraction and a glycerol-based fraction comprising glycerol and water. The liquid-liquid separation can be done by methods known in the art for separating a liquid-liquid two-phase system. Examples of suitable apparatus and methods for liquid-liquid separation include decantation, settling, centrifugation, use of plate separators, use of coalescers, and use of hydrocyclones. Combination of different methods and apparatus may also be used.

The separation step may be carried out at any suitable temperature, in general in the range of 5-95° C. Working below ambient temperature may require cooling operations. On the other hand, a higher temperature may negatively impact the phase separation. Therefore, it may be preferred for the temperature to be at least 10° C., in particular at least 15° C., more in particular at least 20° C. Depending on the circumstances a lower limit of at least 30° C. is also possible. The temperature preferably is at most 70° C., more in particular at most 50° C.

The liquid-liquid separation step results in the formation of a fatty acid methyl ester fraction and a glycerol-based fraction comprising glycerol and water.

The fatty acid methyl ester fraction generally comprises at least 50 wt. % of fatty acid methyl ester, in particular at least 70 wt. %, more in particular at least 80 wt. %. It can be processed as desired. It can, for example, be combined with the biodiesel pool, optionally after further purification, blended with other fuels for use in, e.g., industrial furnaces or boilers, or processed in any other way.

The glycerol-based fraction generally comprises less than 10 wt. % of FAME, in particular less than 5 wt. %. The ratio between water and glycerol in the glycerol-based fraction can vary between wide ranges, dependent on the amount of water present in the starting glycerol and the amount of glycerol evaporated in the partial evaporation step. For example, the glycerol-based fraction can comprise 10-90 wt. % of glycerol, and 90-10 wt. % of water.

The fraction can be processed as desired. In one embodiment it is provided as carbon source to a fermentation process, optionally after having been combined with other fractions, as will be discussed in more detail below. No further purification steps are required on this fraction.

The partial evaporation step resulted in a remainder fraction comprising glycerol. The composition of the remainder fraction will depend on the composition of the starting glycerol fraction.

The partial evaporation step has resulted in the removal of water, fatty acid methyl ester, and methanol. Therefore, the remainder fraction generally comprises less than 5 wt. % of the total of water and methanol, in particular less than 3 wt. %, more in particular less than 1 wt. %. The remainder fraction generally comprises less than 6 wt. % of fatty acid methyl ester, preferably less than 3 wt. %, more preferably less than 1 wt. %.

The remainder fraction may contain non-FAME MONG. Where the non-FAME MONG has a boiling point higher than that of glycerol and fatty acid methyl ester, it will not be removed by partial evaporation, and will be retained in the remainder fraction. The amount of non-FAME MONG present in the remainder fraction may vary within wide ranges. In one embodiment, the remainder fraction comprises 0-35 wt. % of non-FAME MONG. In one embodiment the remainder fraction can comprise 0-10 wt. % of non-FAME MONG, in some cases 0-5 wt. % of non-FAME MONG. In another embodiment, the remainder fraction can comprise 5-35 wt. % of non-FAME MONG, in particular 5-20 wt. % of non-FAME MONG.

The glycerol content of the remainder fraction may vary within wide ranges. It will generally be in the range of 50-100 wt. %, more in particular in the range of 70-100 wt. % glycerol.

As indicated above, the starting glycerol fraction may contain an inorganic salt.

In one embodiment, the performance of the partial evaporation step may result in the formation of a remainder fraction comprising solid salt. This can occur where the removal of water in the partial evaporation step results in a decrease in solubility of the inorganic salts, in particular the sulphate salts, resulting in the formation of solid salts in the remainder fraction. In this embodiment, the remainder fraction may then be subjected to a salt removal step, resulting in a salt fraction and a glycerol-rich fraction. The salt removal step is in essence a solid-liquid separation step, where the solid salt is removed from the liquid phase. Suitable solid-liquid separation steps are known in the art, and include, e.g., settling, sedimentation, filtration, centrifugation and the use of apparatus like hydrocyclones. Combinations of various methods may also be used. Centrifugation may be preferred. It is within the scope of the skilled person to select a suitable method for effecting a solid-liquid separating step.

The resulting glycerol-rich fraction resulting from the salt removal step, generally comprises less than 5 wt. % of inorganic salts, in particular less than 3 wt. %, more in particular less than 1 wt. %. For the amounts of water, methanol, and FAME, reference is made to what is stated above for the remainder fraction.

The glycerol-rich fraction consists for at least 90 wt. % of the total of glycerol and non-FAME MONG, in particular at least 95 wt. %, more in particular at least 98 wt. %. The respective amounts of glycerol and non-FAME MONG in this fraction depend on the amount of non-FAME MONG present in the starting glycerol. In one embodiment, the amount of glycerol is at least 60 wt. %. It may be preferred for the amount of glycerol to be at least 70 wt. %, more in particular at least 80 wt. %. In some embodiments, where the starting material comprises a relatively low amount of non-FAME MONG, the glycerol content may be higher, in particular at least 85 wt. %, or at least 90 wt. % of glycerol, or at least 95 wt. % of glycerol.

The salt fraction resulting from the salt separation step generally comprises at least 50 wt. % or inorganic salts, in particular at least 50 wt. % of sodium sulphate and/or potassium sulphate, more in particular for at least 70 wt. %, still more in particular for at least 80 wt. %. Depending on the method for removing the salt, it may be preferred to have some glycerol remaining in the salt fraction, e.g., to form a slurry. In this case, the amount of glycerol may be, e.g., at least 2 wt. %, in particular at least 5 wt. %, e.g., between 2 and 20 wt. %.

As indicated above, the remainder fraction from the partial evaporation step may contain a substantial amount of non-FAME MONG, e.g., at least 5 wt. %. The same goes for the glycerol-rich fraction resulting from the salt removal step. There may be further glycerol fractions in the process according to the invention which comprise a substantial amount of non-FAME MONG. In one embodiment of the invention, such a fraction which may, e.g., have a non-FAME MONG content of at least 5 wt. %, e.g., between 5 and 35 wt. %, more in particular between 10 and 35 wt. %, can be submitted to a MONG removal step. In one embodiment, the remainder fraction is submitted to a MONG-removal step, optionally after a salt removal step.

There are various possibilities for suitable MONG removal steps. In one embodiment, a MONG removal step encompasses allowing the starting material to settle, and then removing the MONG in as far as it has separated out. In a preferred embodiment, a MONG removal step comprises a centrifugation step where a MONG-containing fraction is subjected to a centrifugation step to form a glycerol-rich bottom fraction, and a MONG-rich top fraction, and a separation step wherein the MONG-rich top fraction is separated from the glycerol-rich bottom fraction.

In one embodiment water is added to the faction to be provided to the MONG-removal step, where the MONG-removal step centrifugation step. The presence of water may result in improved phase separation. If water is added, its amount is preferably limited. In one embodiment water is added to a total water content of the fraction to be provided to the centrifugation step of 1-15 wt. %, in particular 3-10 wt. %. After the MONG removal step, the glycerol-rich fraction and the MONG rich fraction are separated from each other via a liquid-liquid separation step. Liquid-liquid separation steps are known in the art, and require no further elucidation here. Various fractions obtained in the process according to the invention may be processed as desired.

The invention will be illustrated by the figures, without being limited thereto or thereby. It will be clear to the skilled person that the information provided above on the composition of the various fractions and the process conditions applied in the various steps can be combined with the information in the figure descriptions given below.

Further variations on the process according to the invention will also be clear to the skilled person.

In FIG. 1, a starting glycerol fraction comprising glycerol, water, and fatty acid methyl esters is provided through line (1) to an evaporation unit (2), where the glycerol fraction is partially evaporated. The evaporated fraction comprising glycerol, water, and fatty acid methyl esters is withdrawn through line (3), and provided, after condensation, to a liquid/liquid separation unit (4). In liquid-liquid separation unit (4) a fatty acid methyl ester fraction is formed, which is withdrawn through line (5), and a glycerol-based fraction comprising glycerol and water which is withdrawn through line (6). A remainder fraction comprising glycerol is withdrawn from evaporation unit (2) through line (7). The remainder fraction can be processed as desired, and can be provided, e.g., as carbon source to a fermentation process. The glycerol-based fraction (6) from the partial evaporation step can be processed as desired. It can be combined, e.g., with the remained fraction in line (7) through means not shown.

Figure 2:
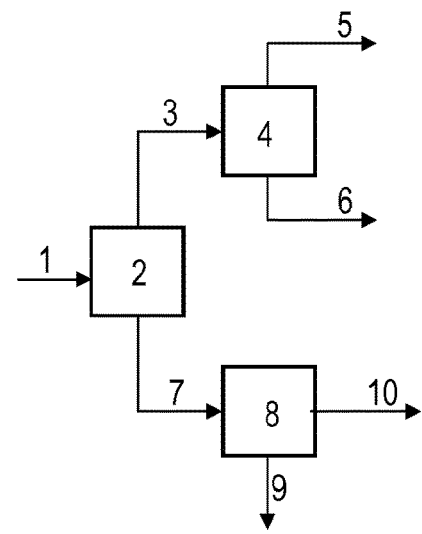
FIG. 2 illustrates a second embodiment of a process according to the invention.

In FIG. 2, a variation on the process of FIG. 1 is shown. Where the starting glycerol fraction additionally comprises inorganic salt, in particular sulphate salts, the remainder fraction comprises glycerol and solid inorganic salt. In this case, the remainder fraction from the distillation unit (2) in line (7) is provided to a salt removal unit (8), where a salt fraction is formed, which is withdrawn through line (9), and a glycerol-rich fraction, which is withdrawn through line (10). The salt removal unit may, e.g., be a filtration step as discussed above. The glycerol rich fraction in line (10) can be processed as desired, and can be provided, e.g., as carbon source to a fermentation process. Again, the glycerol-based fraction (6) from the partial evaporation step can be processed as desired. It can be combined, e.g., with the remained fraction in line (7), or, more preferably, with the glycerol-rich fraction in line (10) through means not shown.

Figure 3:
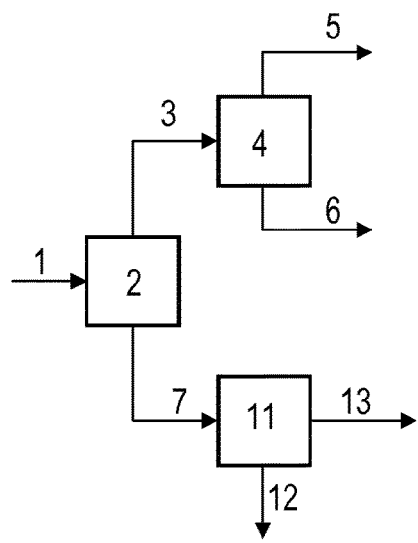
FIG. 3 illustrates a third embodiment of a process according to the invention.
Figure 4:
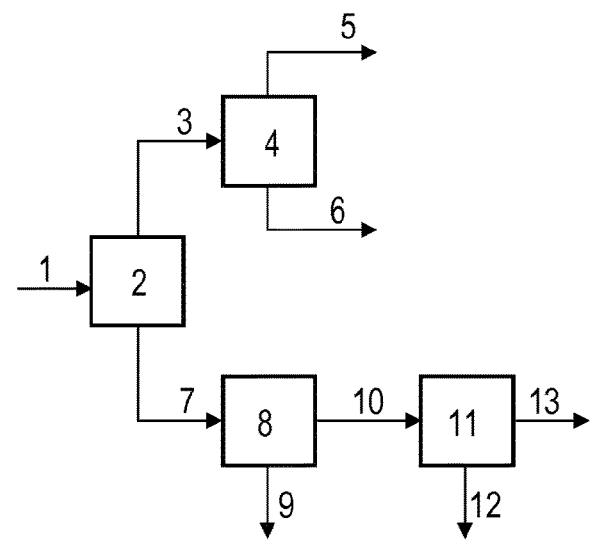
FIG. 4 illustrates a fourth embodiment of a process according to the invention.

FIGS. 3 and 4 provide variations on FIGS. 1 and 2, respectively. In these Figures, a MONG-removal unit (11) is inserted.

In FIG. 3, the remainder fraction that is withdrawn from evaporation unit (2) through line (7) is provided to a MONG removal unit (11). In this unit A MONG-rich fraction is formed, which is withdrawn through line (12). A product glycerol fraction with a reduced MONG content is withdrawn through line (13). This fraction can be processed as desired, and can be provided, e.g., as carbon source to a fermentation process. The glycerol-based fraction (6) from the partial evaporation step can be processed as desired. It can be combined, e.g., with the remained fraction in line (7), or, preferably with the product fraction in line (13) through means not shown.

In FIG. 4, the glycerol rich fraction in line (10) is provided to a MONG removal unit (11). In this unit A MONG-rich fraction is formed, which is withdrawn through line (12). A product glycerol fraction with a reduced MONG content is withdrawn through line (13). This fraction can be processed as desired, and can be provided, e.g., as carbon source to a fermentation process. Again, the glycerol-based fraction (6) from the partial evaporation step can be processed as desired. It can be combined, e.g., with the remained fraction in line (7), more preferably, with the glycerol-rich fraction in line (10), or still more preferably with the product fraction in line (13) through means not shown.

As indicated above, the glycerol product produced in the process according to the invention can be provided as carbon source to a fermentation process, in particular a fermentation process for the manufacture of diols or carboxylic acid salts. Diols which can be obtained through fermentation of glycerol include in particular 1,2-propane diol and 1,3-propane diol. Carboxylic acid salts include in particular salts of succinic acid and propionic acid. Suitable salts include sodium, potassium, calcium, and magnesium salts. In a preferred embodiment, the glycerol product produced in the process according to the invention is be provided as carbon source to a fermentation process for the manufacture of a propionic acid salt, preferably selected from the group of calcium propionate, magnesium propionate, sodium propionate, and potassium propionate, more in particular calcium propionate.

Therefore, in one embodiment of the present invention, the remainder fraction from the partial evaporation step, optionally after a salt removal step, and optionally after a MONG-removal step, and optionally after having been combined with the second fraction comprising glycerol, water, and methanol, is provided as carbon source to a fermentation process, wherein a fermentation medium is fermented by means of a microorganism capable of producing a diol, in particular 1,2-propane diol or 1,3-propane diol, to provide a fermentation broth comprising a diol, in particular 1,2-propane diol or 1,3-propane diol, or wherein a fermentation medium is fermented by means of a microorganism capable of producing a carboxylic acid, in particular succinic acid or propionic acid in the presence of a caustic salt to provide a fermentation broth comprising a carboxylic acid salt, in particular a succinic acid salt or a propionic acid salt.

The invention pertains in particular to a process wherein the remainder fraction from the partial evaporation step, optionally after a salt removal step, and optionally after a MONG-removal step, and optionally after having been combined with the second fraction comprising glycerol, water, and methanol, is provided as carbon source to a fermentation process, wherein a fermentation medium is fermented by means of a microorganism capable of producing propionic acid in the presence of a caustic salt to provide a fermentation broth comprising a propionic acid salt.

In another embodiment, the invention pertains to a process comprising the steps of
  providing a glycerol containing-fraction as carbon source to a fermentation medium;
  fermenting the fermentation medium by means of a microorganism capable of producing a fermentation product to provide a fermentation broth comprising a fermentation product, and
  recovering the fermentation product from the fermentation broth, wherein the glycerol-containing fraction comprises the remainder fraction from the partial evaporation step of the process according to the invention, optionally after a salt removal step, and optionally after a MONG removal step.

For preferred fermentation products reference is made to what is stated above.

It is noted that the product as described above can be provided directly to the fermentation step, without further purification steps being required. More specifically, there will be no intermediate glycerol distillation step between the partial evaporation step and the step of providing the glycerol product as carbon source to a fermentation process.

The fermentation can be carried out by methods known in the art, using microorganisms suitable for the production of the desired fermentation product. Examples of suitable microorganisms for the production of propionic acid include *Propionibacterium*, e.g., *P. acidipropionici*, *P. freudenreichii*, *P. baumani*, and *P. thoenii*. 1,3-propane diol can, e.g., be obtained using a member of the *Enterobacteriaceae*, such as *Klebsiella pneumonia*, *Klebsiella oxytoca*, *Citrobacter freundii*, *Citrobacter werkmanii*, or other organisms like *Escherichia coli*, *Clostridium butyricum*, *Clostridium, pasteurianam*, or *Clostridium acetobutylicum*. 1,2-propane diol can, e.g., be obtained using a suitable *Escherichia coli* or *S. cerevisiae*. Succinic acid can, e.g., be obtained using a suitable *Escherichia coli*. Reference is made to Cheng Li et al., Microbial Conversion of Waste Glycerol from Biodiesel Production into value-added products., Energies 2013, 6, 4739-4768.

It is within the scope of the skilled person to select, using his common general knowledge, a suitable fermentation process, including fermentation conditions, a suitable microorganism, and a suitable broth composition Where the fermentation product is a carboxylic acid, e.g., succinic acid or propionic acid, the formation of the carboxylic acid during the fermentation results in a decrease in pH of the fermentation broth. To counter this and keep the pH within the range where the microorganism can perform, a caustic salt, generally in the form of a solution is typically added during the fermentation. The addition of the salt results in the conversion of the propionic acid generated to the corresponding propionate salt.

Suitable caustic salts include one or more of calcium (hydr)oxide, calcium carbonate, calcium bicarbonate, magnesium (hydr)oxide, sodium hydroxide, ammonium hydroxide, potassium hydroxide, magnesium carbonate, sodium bicarbonate, potassium bicarbonate. Depending on the solubility of the base, the basic solution mentioned above may be a true solution in the sense that the base is completely dissolved and the solution does not contain solid components. However, the basic solution may also be a slurry, which contains solid particles in addition to dissolved base. Within the present specification the word solution is intended to encompass both embodiments. Where the carboxylic acid is propionic acid, the addition of a calcium salt as caustic salt is considered preferred as calcium propionate is a desirable product.

Generally, the basic solution is added in an amount effective to control the pH of the broth between about 3 and 9, more specifically between 6.5 and 8.5.

The fermentation medium will contain other components known in the art such as nitrogen sources, and other constituents.

These do not require further elucidation here.

The glycerol may be used as single carbon source in the fermentation process. It is also possible to possible to combine it with further carbon sources. For the present invention to be attractive, it is generally preferred for the glycerol to make up at least 30 wt. % of the carbon source, preferably at least 50 wt. %, more preferably at least 70 wt. %.

Once the fermentation is completed, the fermentation product salt will be recovered from the fermentation broth.

Generally, the first step in this process is a biomass removal step. This may be carried out in manners known in the art, e.g., via a filtration step or centrifugation step. Efficient biomass removal will improve product quality, including product color.

The resulting product from which biomass has been removed, can be subjected to various further processing steps.

In the following, various processing steps are described for propionic acids. It will be clear to the skilled person which of these steps can be applied in the processing of other fermentation products such as 1,2 propane diol or 1,3 propane diol, or succinic acid.

The product from biomass has been removed can be subjected to one or more of the following processing steps:
  a purification step, wherein an aqueous stream comprising propionic acid and/or propionic acid salt is purified, e.g., by contacting it with activated carbon, and recovering a purified aqueous stream comprising propionic acid and/or propionic acid salt.
  a spray-drying step, wherein an aqueous stream comprising propionic acid and/or propionic acid salt is spray-dried to form a solid powder comprising propionic acid and/or propionic acid salt.
  a concentration step, wherein water is removed from an aqueous stream comprising propionic acid and/or propionic acid salt to yield an aqueous stream comprising propionic acid and/or propionic acid salt with a higher concentration.
  a precipitation step, wherein contaminants are precipitated from an aqueous stream comprising propionic acid and/or propionic acid salt and precipitatable contaminants, e.g., by adjusting the water content and/or the pH of the medium to such a value that the precipitatable contaminants precipitate from the aqueous medium, while the propionic acid and/or propionic acid salt remain in solution.
  a precipitation step, wherein a propionic acid salts is precipitated from an aqueous stream comprising propionic acid and/or propionic acid salt, e.g., by adjusting the water content and/or the pH of the medium to such a value that the propionic acid salt precipitates from the aqueous medium.
  an acidification step, wherein an aqueous medium comprising propionic acid salt is acidified by the addition of an acid to convert the propionic acid salt into propionic acid.
  an extraction step, wherein an aqueous medium comprising propionic acid is contacted with an organic liquid which is not miscible with water, followed by a phase separation step, wherein the organic liquid comprising propionic acid is separated from an aqueous liquid in which the propionic acid concentration has been reduced.

All steps above are in themselves known in the art. It is within the scope of the skilled person to apply them, separately or in combination, to an aqueous stream comprising propionic acid and/or propionic acid salt. No further elucidation is required. As indicated above, it will be clear to the skilled person if and how the various steps can be applied to other fermentation products, including 1,2-propane diol, 1,3-propane diol, and succinic acid and/or succinic acid salts. No further elucidation is required.

Preferred processing sequences for recovering propionic acid salt from the fermentation broth are the following:

In a first processing sequence the step of recovering propionic acid salt from the fermentation broth encompasses the sequential steps of biomass removal, optional purification with activated carbon, optionally a concentration step, and spray drying.

In a further processing sequence the step of recovering propionic acid salt from the fermentation broth encompasses the sequential steps of biomass removal, optional purification with activated carbon, a concentration step, an optional precipitation step wherein contaminants are precipitated, and a precipitation step wherein a propionic acid salt is precipitated. This latter step may also be indicated as a crystallization step.

In a further processing sequence the step of recovering propionic acid salt from the fermentation broth encompasses the sequential steps of biomass removal, optional purification with activated carbon, an optional concentration step, an acidification step, and an extraction step.

It has been found that if a glycerol rich fraction prepared as described above is used as carbon source in a glycerol fermentation, the resulting fermentation broth can be processed to relatively pure products. In particular, it has been found that products may be obtained which show less contamination, and/or which show a good stability in that they do not develop undesirable odors, as sometimes occurs when crude glycerol is used as starting material.

It will be clear to the skilled person that preferred embodiments of the various process steps can be combined.

The invention will be elucidated with reference to the following examples, without being limited thereto or thereby.

Determination of Fatty Acid Methyl Esters (FAME) via GC/MS

GC/MS Conditions:

| | |
|---|---|
| GC | Trace GC Ultra |
| Column | VF-1 MS, L = 30 m, i.d. = 0.25 mm, df = 0.25 μm |
| Oven temp. | 50° C. - 6 min - 11° C./min - 275° C. - 3.5 min |
| Carrier gas | helium, constant flow 1.0 ml/min with vacuum compensation |
| Injector | PTV-injector |
| Inlet temperature | 250° C. |
| Injection type | split, splitflow 75 ml/min |
| Injection volume | 0.5 μl |
| Detector 1 | Trace DSQ mass spectrometer |

MS Conditions:

| | |
|---|---|
| Emission current | 100 μA |
| Detector gain | 3.00*105 |
| Ionisation energy | −70 eV |
| Source temp. | 250° C. |
| Interface temp. | 285° C. |
| Mass range | 30-300 |
| Scan rate | 1000 amu/s |
| Cryo 915 settings: Constant temp.: | 220° C. |

Sample Preparation:

Dissolve 0.05 g of sample in 5 g of a solution of 75 mg/kg tridecanoic acid in THF.

Pipette 900 μl of the solution in a 2 ml glass vial and add 100 μl of BSTFA. Cap the vial.

Heat the vial for 2 minutes at 70° C.

Standards:

Prepare standards, containing a known amount of the fatty acid methyl esters of interest, in the same way as the samples

EXAMPLE 1

A crude glycerol fraction comprising water, methanol, fatty acid methyl esters, and glycerol was subjected to a partial distillation step, resulting in an evaporated fraction comprising water, methanol, fatty acid methyl esters, and glycerol. Upon condensation, a liquid was formed in which phase separation occurred. A yellow top layer and a transparent/yellowing bottom layer were formed. The two phases were separated using a separation funnel, and 887 grams of the bottom layer, and 270 grams of the top layer were collected. The bottom layer appears to be a glycerol-containing fraction, while the top layer appears to be a FAME fraction.

The invention claimed is:

1. Process for manufacturing purified glycerol comprising the steps of
   providing a starting glycerol fraction comprising glycerol, water, and fatty acid methyl esters,
   subjecting the glycerol fraction to a partial evaporation to form an evaporated fraction comprising glycerol, water, and fatty acid methyl esters, and a remainder fraction comprising glycerol,
   condensing the evaporated fraction to form a liquid,
   subjecting the liquid evaporated fraction comprising glycerol, water, and fatty acid methyl esters to a liquid-liquid separation step, resulting in the formation of a fatty acid methyl ester fraction that comprises at least 50 wt. % of fatty acid methyl ester and a glycerol-based fraction comprising glycerol and water.

2. Process according to claim 1, wherein the starting glycerol fraction comprises water in an amount of 1-30 wt. %, and/or fatty acid methyl esters in an amount of 1 to 20 wt. %.

3. Process according to claim 1, wherein the partial evaporation step is carried out by flash evaporation or by partial distillation.

4. Process according to claim 1, wherein the composition of the evaporated fraction is as follows: a glycerol content in the range of 25 to 90 wt. %, a fatty acid methyl ester content in the range of 1 to 20 wt. %, a water content in the range of 5 to 40 wt. %, a methanol content in the range of 0 to 6 wt. %, wherein as compared to the starting glycerol fraction, the evaporated fraction has a lower glycerol content, a higher water content, a higher FAME content, and if present, a higher methanol content.

5. Process according to claim 1, wherein the glycerol-based fraction derived from the liquid-liquid separation step comprises 10-90 wt. % of glycerol and 90-10 wt. % of water and/or less than 10 wt. % of FAME.

6. Process according to claim 1, wherein the remainder fraction comprises less than 5 wt. % of the total of water and methanol, and/or less than 6 wt. % of fatty acid methyl ester.

7. Process according to claim 1, wherein the starting glycerol fraction comprises an inorganic salt, and the remainder fraction comprises glycerol and solid salt, and the remainder fraction is subjected to a salt removal step, resulting in a salt fraction and a glycerol-rich fraction.

8. Process according to claim 5, wherein the starting glycerol fraction comprises an inorganic salt in an amount of 2-15 wt. %.

9. Process according to claim 1 wherein the remainder fraction comprises non-FAME MONG, and the remainder fraction is submitted to a MONG-removal step, optionally after a salt removal step.

10. Process according to claim 9, wherein the remainder fraction has a non-FAME MONG content of at least 5 wt. %, wt. %.

11. Process according to claim 9, wherein the MONG removal step comprises a centrifugation step where a MONG-containing fraction is subjected to a centrifugation step to form a glycerol-rich bottom fraction, and a MONG-rich top fraction, and a separation step wherein the MONG-rich top fraction is separated from the glycerol-rich bottom fraction.

12. Process according to claim 1, wherein the remainder fraction from the partial evaporation step, optionally after a salt removal step, and optionally after a MONG-removal step, and optionally after having been combined with the second fraction comprising glycerol, water, and methanol, is provided as carbon source to a fermentation process, wherein a fermentation medium is fermented by means of a microorganism capable of producing a diol, to provide a fermentation broth comprising a diol, or wherein a fermentation medium is fermented by means of a microorganism capable of producing a carboxylic acid.

13. Process according to claim 12, wherein the microorganism is capable of producing propionic acid, and the fermentation broth comprises a propionic acid salt.

* * * * *